United States Patent
Wu et al.

(10) Patent No.: US 10,532,231 B2
(45) Date of Patent: Jan. 14, 2020

(54) HAIR CARE COMPOSITION COMPRISED OF BIO-MODIFIED NATURAL SURFACTANTS AND CATIONIC MOLECULAR NETWORK

(71) Applicant: Draco Natural Products Inc, San Jose, CA (US)

(72) Inventors: Jerry Wu, San Jose, CA (US); James-Jianguo Chen, San Jose, CA (US); Dong Li, San Jose, CA (US)

(73) Assignee: Draco Natural Products Inc., San Jose, CA (US)

( * ) Notice: Subject to any disclaimer, the term of this patent is extended or adjusted under 35 U.S.C. 154(b) by 0 days.

(21) Appl. No.: 16/127,623

(22) Filed: Sep. 11, 2018

(65) Prior Publication Data

US 2019/0001162 A1    Jan. 3, 2019

Related U.S. Application Data

(63) Continuation of application No. 15/158,418, filed on May 18, 2016, now abandoned, which is a continuation-in-part of application No. 14/593,651, filed on Jan. 9, 2015, now abandoned.

(51) Int. Cl.
*A61Q 5/02* (2006.01)
*A61K 8/9706* (2017.01)
*A61Q 5/12* (2006.01)

(52) U.S. Cl.
CPC .............. *A61Q 5/02* (2013.01); *A61K 8/9706* (2017.08); *A61Q 5/12* (2013.01); *A61K 2800/85* (2013.01)

(58) Field of Classification Search
CPC .......... A61Q 5/02; A61Q 5/12; A61K 8/9706; A61K 2800/85
See application file for complete search history.

(56) References Cited

U.S. PATENT DOCUMENTS

2010/0144892 A1*  6/2010  Wu .................. A21D 13/04
514/738

* cited by examiner

*Primary Examiner* — Trevor Love
(74) *Attorney, Agent, or Firm* — Helen Mao; Imperium Patent Works

(57) ABSTRACT

Natural haircare ingredient composition and haircare compositions containing such natural haircare ingredient compositions are provided. In one novel aspect, the natural hair ingredient composition is provided which comprises *candida Krusei* mediated bio-modification of marine organism and plants including bio-modified natural marine surfactants, three-dimensional molecular framework, and natural mineral salts. In one embodiment, the natural surfactants are produced from natural marine organisms such as brown algae, sea kelp, sponge, brown seaweeds, and red seaweeds by *candida Krusei* mediated bio-modification. In another novel aspect, a haircare composition comprises about 10% of the natural haircare ingredient composition, by weight of the haircare composition. In one novel aspect, *Candida Krusei* bio-modification process is used. Natural polymeric compounds in the marine plants are modified during the process resulting in three-dimensional molecular framework.

12 Claims, No Drawings

HAIR CARE COMPOSITION COMPRISED OF BIO-MODIFIED NATURAL SURFACTANTS AND CATIONIC MOLECULAR NETWORK

CROSS REFERENCE TO RELATED APPLICATIONS

This application is a continuation, and claims priority under claims priority under 35 U.S.C. § 120 from nonprovisional U.S. patent application Ser. No. 15/158,418, entitled "HAIR CARE COMPOSITION COMPRISED OF BIO-MODIFIED NATURAL SURFACTANTS AND CATIONIC MOLECULAR NETWORK," filed on May 18, 2016, the subject matter of which is incorporated herein by reference. Application Ser. No. 15/158,418 in turn is a continuation-in-part of, and claims priority under 35 U.S.C. § 120 from nonprovisional U.S. patent application Ser. No. 14/593,651, entitled "HAIR CARE COMPOSITION COMPRISED OF NATURAL SURFACTANTS AND CATION," filed on Jan. 9, 2015, the subject matter of which is incorporated herein by reference.

TECHNICAL FIELD

The disclosed embodiments relate generally to hair care compositions, and, more particularly, to hair care compositions using bio-modified cationic molecular network.

BACKGROUND

Hair care is important for reasons other than just appearance. While healthy looking locks are aesthetically appealing, it is also an important aspect of one's overall physical maintenance regimen, just like skins and eyes. Human hairs have large mass of fibers serving to catch soil from the surrounding environment. Added to this is sebum, the natural oil that is released onto the hair at its base from the sebaceous gland of each follicle. Hair care products, such as shampoo and conditioner, are designed to remove dirt and soil and then condition the hair. As people wash their hair more frequently, sebum rarely coats the whole length of the hair fibers, resulting in high demand for better hair conditioning form of the shampoo and/or conditioner.

The detersive effect of shampoo comes from surfactants that are capable of bringing hydrophobic wastes to the aqueous phase to be washed away. A majority of such surfactants are either sulfates or long chain carboxylates of metal salts. Existing technologies focus on synthetic surfactants that rely heavily on petrochemicals and other chemicals. Synthetic materials for hair care products not only are environmentally unfriendly but also are harsh to skins. Natural surfactants are better alternatives to synthetic ones. U.S. Pat. No. 8,557,311 [1] discloses a natural surfactant derived from gynostemma extract that can be used as surfactant/cleaning agent/emulsifier/foaming agent. It claims that such an extract has distinctive surface tension altering functions, which reduce the surface tension of aqueous solutions and allow foam formation and emulsification with oil, dirt and other water insoluble substances.

The main aim of the shampoo is to remove dirt and soil. Conditioners are applied either separately after shampoo or together with shampoo, such as in the 2-in-1 products. After applying the conditioners, a short time, for example, thirty seconds to a couple of minutes, is required before rinsing the conditioners out. The stay time allows the primary conditioning agents including quaternized surfactants, cationic polymers, to be bound to the hair such that it is left behind on the surface of the hair to provide the protection. In practice, the faster the bounding, the shorter time is required for the conditioner to stay before rinsed out, and the more convenient is for the user. The current synthetic compositions require around one to ten minutes to complete the bounding.

Improvements are needed in seeking natural ingredients for healthier hair care products and compositions that shorten the stay-time requirement for the hair care products.

SUMMARY

The present invention is directed to natural haircare ingredient composition and haircare compositions containing such natural haircare ingredient compositions. In one novel aspect, the natural hair ingredient composition is provided which comprises *candida krusei* mediated bio-modified marine surfactants and cationic molecular network from marine organism and plants, and natural mineral salts. The amount of the bio-modified marine surfactants and cationic molecular network in the composition may be ranged from about 0.1% to 60% by weight, preferably about 1% to 30% by weight. The natural mineral salts in the composition are no less than 1% by weight.

In one embodiment, the marine surfactants and cationic molecular network is produced from natural marine organisms such as brown algae, sea kelp, sponge, brown seaweeds, and red seaweeds by *candida krusei* mediated bio-reaction.

In another embodiment, the natural mineral salts are one or more salts selected from the group consisting of: sodium, potassium, calcium, magnesium, strontium, with chloride, bromide, bicarbonate, fluoride, sulfate, borate, iodide.

In one embodiment, the natural haircare ingredient composition further comprises from about 0.01% to about 5% of supercritical extracted natural oil and fluid, by weight of the natural haircare ingredient composition, preferably about from about 0.1% to about 2% of supercritical extracted natural oil and fluid. In another embodiment, the supercritical extracted natural oil and fluid is formed by one or more combinations selected from the group consisting of sea buckthorn oil with rosemary antioxidant liquid, lavender oil with rosemary antioxidant liquid, and supercritical extracted daikon seed oil with clove antioxidant liquid.

In one novel aspect, haircare compositions contain natural haircare ingredient composition. In one embodiment, the natural ingredient composition is fast acting and thereby, reduces the stay-time needed for haircare composition. In one embodiment, the haircare compositions are for shampoos. In another embodiment, the haircare compositions are for conditioners. In yet another embodiment, the haircare compositions are for 2-in-1 haircare products.

DETAILED DESCRIPTION

Reference will now be made in detail to some embodiments of the invention, examples of which are illustrated in the accompanying drawings.

Using natural ingredients for hair care products not only benefits environmental protection but also offers better treatment for the hair by alleviating the harshness of the synthetic materials on the hair and the skin. In one novel aspect of the current invention, haircare ingredient compositions are made primarily of natural surfactants, natural conditioning agent, natural deposition aid and natural viscosity modifier. In another novel aspect of the current invention, the natural ingredient composition is fast acting and thereby, reduces the stay-time needed for the conditioner. In one embodiment, the natural ingredient composition can form the gel bonding to the hair from 0.1 second to ten seconds, greatly reducing the stay-time needed if used in hair care products such as shampoos, conditioners or 2-in-1 products.

In one novel aspect, a natural hair ingredient composition is provided which comprises bio-modified marine surfactants from marine plants and organisms, natural mineral salts and cationic molecular network. The amount of the bio-modified marine surfactants in the composition may be ranged from about 0.1% to 60% by weight, preferably about 1% to 30% by weight. The natural mineral salts in the composition are no less than 1% by weight. The cationic molecular network in the composition is about 0.1% to 50% by weight, preferably about 1% to 35% by weight.

In one embodiment, the bio-modified marine surfactants are produced from natural marine organisms such as brown algae, sea kelp, sponge, brown seaweeds, and red seaweeds. Marine surfactants are unique in that they are rich in polymers with carboxylate and sulfate moieties. Research discovers that marine polysaccharides widely exist in marine organisms. According to different sources, marine polysaccharides can be divided into different types, such as marine animal polysaccharides, plant polysaccharides, and microbial polysaccharides. Plant polysaccharides are the most abundant polysaccharides in marine organisms, such as seaweeds, occurring from the tide level to considerable depths free-floating or anchored. Moreover, seaweed contains high percentages of polysaccharide, accounting for more than 50% of dry weight, making it a great source to develop natural compositions for hair care products.

A variety of marine plant organisms, especially seaweeds, can be used to provide natural ingredients for healthier hair care products because they possess the special characteristics of high sulfation and carboxylation.

Brown seaweed, for example, is rich in alginates and fucans. Alginates, the major constituent of brown seaweeds' cell walls are linear acidic polysaccharides composed with a central backbone of poly-D-glucuronic acid (G blocks), poly-D-mannuronic acid (M blocks) and alternate residues of D-guluronic acid and D-mannuronic acid (GM blocks) [Jinchen Sun and Huaping Tan, *Alginate-Based Biomaterials for Regenerative Medicine Applications*, Materials, 2013, 6, 1285-1309]. Fucans are also one of the major constituents of brown seaweed cell walls, and are ramified sulfated polysaccharides constituted by a central backbone of fucose sulfated in positions C2 and/or C4 and ramifications at each two or three fucose residues [Wei Wang, Shi-Xin Wang, and Hua-Shi Guan, *The Antiviral Activities and Mechanisms of Marine Polysaccharides: An Overview*, Mar. Drugs 2012, 10, 2795-2816].

Red seaweed possesses carrageenans, the sulfated D-galactans. Red seaweed polysaccharides are primarily classified as agarans and carrageenans based on their stereochemistry. Carrageenans are sulfated D-galactans composed of repeating disaccharide units with alternating 3-linked β-D-galactopyranose (G-units) and 4-linked α-D-galactopyranose (D-units) or 3,6-anhydro-α-galactopyranose (AnGal-units) [Jinchen Sun et al.].

Marine animal polysaccharides, just like marine plant polysaccharides, are rich in carboxylates and sulfates while being widely available in marine animal sources. For example, rosacelose, a glucose and fucose sulfate can be isolated from the aqueous extract of the marine sponge Mixylla rosacea. This marine polysaccharide has a linear polysaccharide structure mainly composed of 4,6-disulfated 3-0-glycosylated α-D-glucopyranosyl, and 2,4-disulfated 3-0-glycosylated α-L-fucopyranosyl residues (in a 3:1 molar ratio) [Jinchen Sun et al.], [Cimino, P.; Bifulco, G.; Casapullo, A.; Bruno, I.; Gomez-Paloma, L.; Ricco, R. *Isolation and NMR characterization of rosacelose, a novel sulfated polysaccharide from the sponge Mixylla rosacea*. Carbohydr. Res. 2001 334, 39-47].

In accordance with embodiments of the current invention, combination of Bio-modified marine surfactants from marine organisms forms natural and healthy anionic surfactants that can be used in hair care products. Non-limiting examples of anionic surfactants are marine compounds containing carboxylates and sulfates moieties such as rosacelose, a glucose and fucose sulfate from the aqueous extract of the marine sponge Mixylla rosacea; Alginates, a major constituent of brown seaweeds' cell walls and are linear acidic polysaccharides composed with a central backbone of poly-D-glucuronic acid (G blocks), poly-D-mannuronic acid (M blocks) and alternate residues of D-guluronic acid and D-mannuronic acid (GM blocks); fucans, another major constituents of brown seaweed cell walls, are ramified sulfated polysaccharides constituted by a central backbone of fucose sulfated in positions C2 and/or C4 and ramifications at each two or three fucose residues; and carrageenans, sulfated D-galactans from red seaweed. Preferred amount of these surfactants ranges from about 0.1% to about 60% by weight, more preferably from about 3% to about 50%, even more preferably from about 5% to about 30%.

These Bio-modified marine surfactants often come along with other nutrients, such as mineral salts and polysaccharides, in the form of extracts. Studies show that seaweed extracts have benefits for skin [Choi J S, Moon W S, Choi J N, Do K H, Moon S H, Cho K K, Han C J, Choi I S, *Effects of seaweed Laminaria japonica extracts on skin moisturizing activity in vivo*, J Cosmet Sci. 2013 May-Jun, 64(3): 193-205]. These nutrients in hair care products are beneficial to hair as well.

Marine products are also rich in mineral salts that are incorporated in these natural extracts. Besides acting as natural viscosity modifier, these mineral salts are reported to have skin-moisturizing effect [Z. Ma'or, G. Meshulam-Simon, S. Yehuda, J. A. Gavrieli, *Antiwrinkle and skin-moisturizing effects of a mineral-algal-botanical complex*, Journal of the Society of Cosmetic Chemists, Vol. 51, No. 1, 27-36]. Non-limiting examples of these minerals are sodium chloride, potassium chloride, magnesium chloride, sodium bromide, sodium iodide. These minerals and salts can range from about 1% to 90% depending on the source of the marine surfactants.

Cationic deposition is an important ingredient for conditioning the hair. In general, hair conditioners contain a variety of conditioning and moisturizing ingredients that are left behind on the hair after rinsing and affect the hair characteristics. Cationic surfactants and cationic polymers remain on the hair via electrostatic interactions. They are positively charged when placed in a solution of water. They are attracted to the negatively charge, damaged protein sites on the hair and thereby provides protections and repairs to the hair. When left on the hair, these ingredients coat the fibers and counteract the problem characteristics of the hair.

In one embodiment, the cationic molecular network comes from *candida krusei* mediated bio-modification of marine plants and organisms. The dosage of cationic molecular network could be reduced greatly owing to the three dimensional network that can promote the formation of coacervate micelles easily. Preferred amount of these cationic molecular network ranges from about 0.01% to about 5% by weight, more preferably from about 0.1% to about 2% by weight.

Other natural ingredients can be added to the composition to provide more nutrients to the haircare composition. The combination of supercritical extracted daikon seed oil and rosemary antioxidant liquid is a perfect example of natural conditioning fluid that gives the hair its natural shininess, smoothness, and manageability; and protects the hair from oxidative damage. Other non-limiting examples of such combinations are supercritical extracted sea buckthorn oil with rosemary antioxidant liquid, lavender oil with rosemary antioxidant liquid, supercritical extracted daikon seed oil with clove antioxidant liquid. It is obvious to those skilled in the art that any combinations of natural oils and antioxidant liquid that achieves such effects are within the scope of this invention. Preferred amount of such combination ranges from about 0.1% to about 10% by weight, more preferably from about 1% to about 5% by weight.

Using naturally extracted ingredients for haircare compositions is not only environmentally friendly but also provides better nutrition and protections to the hair. These natural compositions are made primarily of natural surfactants, natural conditioning agent, natural deposition aid and natural viscosity modifier. Adding these naturally extracted ingredients to a haircare composition base produces an eco-friendly and healthier haircare product. The haircare product can be, and not limited to, shampoos, conditioners or 2-in-1 haircare products.

The following example is only for illustrative purpose. Though the following uses shampoo as an example, it is understood by one of ordinary skills in the art it can apply to other types of hair care products, such as conditioners and 2-in-1 haircare products. It does not in any mean to limit the scope of this invention. It is obvious to those skilled in the art that variations to the following example would achieve the same results so as to be within the scope of this invention.

EXAMPLE 1

A shampoo formulation containing the following ingredients was prepared: about 77% water, about 10% *candida krusei* modified natural ingredients composition from this invention for cleansing and deposition promotion, about 3% triethanolamine lauryl sulfate, about 2% Coco alkyldimethyl betaines, both for cleaning and foaming; about 1% preservative, about 4% citric acid for pH adjusting, about 0.5% poly(dimethylsiloxane) for lubricating, about 0.5% cocoyl sarcosine for cleansing, about 2% ethylene glycol distearate for shinning.

EXAMPLE 2

A shampoo formulation containing the following ingredients was prepared: about 77% water, about 10% *candida krusei* modified natural ingredients composition from this invention for cleansing and deposition promotion, 3% sodium laureth sulfate, about 2% ammonium lauryl sulfate, both for cleaning and foaming; about 1% preservative, about 4% citric acid for pH adjusting, about 0.5% emulsifying silicone oil for lubricating, about 0.5% cocamide monoethanolamine for cleansing, about 2% ethylene glycol distearate for shinning.

EXAMPLE 3

A body wash lotion formulation containing the following ingredients was prepared: about 52% water, about 5% cocoamidopropyl Betaine, 8% sodium laureth sulfate, and 20% sodium N-lauroylsarcosinate for cleansing, about 2.5% acrylate copolymer emulsion as emulsifier, about 1% *candida krusei* modified natural ingredients composition from this invention for cleansing and deposition promotion, about 2% Macrogol 4000, about 5% sorbitol, about 2% ethylene glycol distearate, 0.6% 16-18 alcohols, and 2% dodecanoic acid for lubricating, appropriate amount of essence/antiseptic/salt/citric acid.

EXAMPLE 4

A facial cleanser formulation containing the following ingredients was prepared: about 59% water, about 15% cocoamidopropyl Betaine and 15% sodium laureth sulfate for cleansing, about 6% acrylate copolymer emulsion as emulsifier, about 1% *candida krusei* modified natural ingredients composition from this invention for cleansing and deposition promotion, about 3% poly(methyldisiloxane) and 1% ethylene glycol distearate for lubricating, appropriate amount of essence/antiseptic/salt/citric acid.

In one novel aspect, bio-modified three-dimensional marine surfactants and cationic molecular framework produced by *candida krusei* modification of marine plant extract. The resulted bio-modified three-dimensional marine surfactants and cationic molecular framework has the benefit of fast acting function in hair care products. The three-dimensional framework can automatic accumulate and trap conditioning agent on hair so less conditioning agent is needed; it is both economic and time saving.

In another novel aspect, *Candida krusei* mediated bio-modification is applied on marine plants. Marine plants, including, but not limited to, brown algae, sea kelp, sponge, brown seaweeds, and red seaweeds, are reacted with *Candida krusei*. Natural polymeric compounds in these marine plants are modified during the process, resulting in a three-dimensional molecular framework that is used as an essential component for hair care product.

The three-dimensional molecular framework ingredients produced from the reaction of *candida krusei* with the natural marine plants are beneficial when used in the hair product and other skin care products. For example, kelp extraction using the *Candida krusei* mediated bio-modification process results in a unique three-dimensional molecular framework, which provides instantaneous flocculation when used as a hair care product. Flocculation is a phenomenon that refers to the floc particles coalescing into large flocs through the process of adsorption, crosslinking, netting, and aggregation. The technology has the ability to efficiently separate 99.9% non-aqueous substances from sewage. It is the best-known wastewater treatment so far. Flocculation changes the traditional washing principle; avoids the contrast between shampoo and conditioner; and brings a revolutionary design in hair formulations.

The three-dimensional molecular framework ingredients are beneficial when used in hair care products and other molecular framework ingredients. In one novel aspect, the three-dimensional molecular framework ingredients are generated through a *Candida krusei* mediated bio-modification. In particular, *Candida krusei* is added to a bio-modification process to extract ingredients from materials, such as the natural marine organism and plants, including but not limited to, brown algae, sea kelp, sponge, brown seaweeds, and red seaweeds.

In one embodiment, the natural ingredients are extracted using the following procedure. Step one is the cell wall breaking phase. During the cell wall breaking phase, marine plants are grinded and suspended in water in a bioreactor and agitated will high shear force to break their cell walls to form a uniform suspension. Step two is the sterilization phase. During the sterilization phase, the suspension is sterilized by steam to kill microbes and deactivate enzymes that may be present. Step three is the inoculation phase. During the inoculation phase, the sterile suspension is then inoculated by the addition of *Candida Krusei*. Step four is the bio-modification phase. During the bio-modification phase, the bio-reaction runs at 30-38° C. for 24-48 hours, Natural polymeric compounds in these marine plants are modified during the process, resulting in high efficient natural marine surfactants and three-dimensional molecular framework. Step five is the filtration phase. During filtration phase, the plant debris and reaction residues are separated and removed as solids by an ultra-filtration system. Step six is the high temperature short time (HTST) phase. During the HTST phase, the liquid phase is collected and fixed by HTST to deactivate *Candida Krusei*.

Although the present invention has been described in connection with certain specific embodiments for instructional purposes, the present invention is not limited thereto. Accordingly, various modifications, adaptations, and combinations of various features of the described embodiments can be practiced without departing from the scope of the invention as set forth in the claims.

REFERENCES (INCORPORATED HEREIN BY REFERENCE)

1. Jinchen Sun and Huaping Tan, *Alginate-Based Biomaterials for Regenerative Medicine Applications*, Materials, 2013, 6, 1285-1309
2. Wei Wang, Shi-Xin Wang, and Hua-Shi Guan, *The Antiviral Activities and Mechanisms of Marine Polysaccharides: An Overview*, Mar. Drugs 2012, 10, 2795-2816
3. Choi J S, Moon W S, Choi J N, Do K H, Moon S H, Cho K K, Han C J, Choi I S, *Effects of seaweed Laminaria japonica extracts on skin moisturizing activity in vivo*, J Cosmet Sci. 2013 May-Jun, 64(3):193-205
4. Z. Ma'or, G. Meshulam-Simon, S. Yehuda, J. A. Gavrieli, *Antiwrinkle and skin-moisturizing effects of a mineral-algal-botanical complex*, Journal of the Society of Cosmetic Chemists, Vol. 51, No. 1, 27-36
5. Cimino, P.; Bifulco, G.; Casapullo, A.; Bruno, I.; Gomez-Paloma, L.; Ricco, R. *Isolation and NMR characterization of rosacelose, a novel sulfated polysaccharide from the sponge Mixylla rosacea*. Carbohydr. Res. 2001 334, 39-47

What is claimed is:

1. A method, comprising:
   a cell wall breaking phase, wherein during the cell wall breaking phase, marine plants are grinded and suspended in water in a bioreactor and agitated with high shear force to break their cell walls to form a uniform suspension;
   a sterilization phase, wherein the suspension is sterilized by steam to kill microbes and deactivate enzymes that may be present;
   an inoculation phase, wherein the sterile suspension is subsequently inoculated by the addition of *Candida Krusei*;
   a bio-modification phase, wherein the bioreactor runs at 30-38° C. for 24-48 hours, and wherein Natural polymeric compounds in the marine plants are modified resulting in three-dimensional molecular framework;
   a filtration phase, wherein plant debris and reaction residues are separated and removed as solids by an ultra-filtration system from a liquid phase; and
   a high temperature short time (HTST) phase, wherein the liquid phase is collected and fixed by HTST to deactivate *Candida Krusei*.

2. The method of claim 1, wherein the marine plants are selected from the group consisting of brown algae, sea kelp, sponge, brown seaweeds, and red seaweeds.

3. The method of claim 1, wherein the resulted three-dimensional molecular framework is a three-dimensional marine based surfactant and cationic molecular network, and wherein after the filtration phase and the HTST phase the resulting amount of surfactant is about 0.1% to about 60% by weight of a natural hair care composition.

4. The composition of claim 3, wherein the natural hair care composition further comprises more than 1% of natural mineral salts by weight of the natural hair care ingredient composition.

5. The method of claim 4, wherein the natural hair care composition comprises about 3% to about 50% surfactant by weight of a natural hair care composition.

6. The method of claim 4, wherein the natural hair care composition comprises about 5% to about 30% surfactant by weight of a natural hair care composition.

7. The method of claim 4, wherein the natural hair care comprises further comprises from about 1% to 90% of natural mineral salts by weight of the natural haircare ingredient composition.

8. The method of claim 4, wherein the natural mineral salts are one or more ingredients selected from the group consisting of: sodium chloride, potassium chloride, magnesium chloride, sodium bromide, sodium iodide from marine products.

9. The method of claim 4, wherein the natural haircare composition comprises from about 0.1% to about 2% of cationic molecular network by weight of the natural hair care ingredient composition.

10. The method of claim 4, further comprising: from about 0.01% to about 5% of supercritical extracted natural oil and fluid by weight of the natural hair care ingredient composition.

11. The method of claim 10 comprising from about 0.1% to about 2% of supercritical extracted natural oil and fluid, by weight of the natural hair care ingredient composition.

12. The method of claim 10, wherein the supercritical extracted natural oil and fluid is formed by one or more combinations selected from the group consisting of sea buckthorn oil with rosemary antioxidant liquid, lavender oil with rosemary antioxidant liquid, and supercritical extracted daikon seed oil with clove antioxidant liquid.

* * * * *